(12) United States Patent
Fitzgerald et al.

(10) Patent No.: US 6,911,328 B2
(45) Date of Patent: Jun. 28, 2005

(54) METHOD FOR PRODUCING 2,3-DIMETHYL-2,3-DINITROBUTANE AND PRODUCT THEREBY

(75) Inventors: Angel A. Fitzgerald, Fredericksburg, VA (US); Alfredo N. Rayms-Keller, Fredericksburg, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 113 days.

(21) Appl. No.: 10/235,402

(22) Filed: Sep. 4, 2002

(65) Prior Publication Data

US 2004/0043461 A1 Mar. 4, 2004

(51) Int. Cl.$^7$ .......................... C12P 13/00; C07C 205/00
(52) U.S. Cl. ........................ 435/128; 435/41; 435/192; 568/944
(58) Field of Search .................... 435/128, 41, 192; 568/944

(56) References Cited

U.S. PATENT DOCUMENTS

| | | | |
|---|---|---|---|
| 3,957,424 A | 5/1976 | Zefferen et al. ............... | 8/401 |
| 4,503,153 A | 3/1985 | Geigert et al. ............... | 435/147 |
| 4,900,671 A | 2/1990 | Pokora et al. ............... | 435/156 |
| 5,188,953 A | 2/1993 | Johnson et al. ............. | 435/156 |
| 5,391,488 A | 2/1995 | Johnson et al. ............. | 435/147 |
| 5,508,180 A | 4/1996 | Johnson et al. ............. | 435/128 |
| 5,541,091 A | 7/1996 | Wheeler et al. ............ | 435/128 |
| 5,811,584 A | 9/1998 | O'Neill et al. .............. | 564/494 |
| 5,973,203 A | 10/1999 | Egraz et al. ................. | 564/135 |

OTHER PUBLICATIONS

Fiala et al (Mutation Research 179:15–22 (1987)).*

Kenar, James A. "Peroxidase–Catalyzed Synthesis of Energetic Materials. Synthesis of 2,3–Dimethyl–2,3–Dinitrobutane (DMDNB): A Detection Agent for Moldable Explosives." Unpublished (internal report for NSWC Indian Head, NSWC Dahlgren and Office of Naval Research) report from Naval Surface Warfare Center Indian Head Division to Office of Naval Research, Dec. 1999.

Hiner, A. N. P.; Rodriguez–Lopez, J. N.; Arnao, M. B.; Lloyd Raven, E.; Garcia–Canovas, F.; Acosta, M. *Biochem. J.* 2000, 348, 321–328.

Porter, D. J.; Bright, H. J. The Mechanism of Oxidation of Nitroalkanes by Horeradish Peroxidase, *J. Biol. Chem.* 1983, 258, 9913–9924.

Rodriguez–Lopez, J. N.; Hernandez–Ruiz, J.; Garcia–Canovas, F.; Thorneley, R. N. F.; Acosta, M.; Arnao, M. B. *J. Biol. Chem.* 1997, 272, 5469–5476.

* cited by examiner

*Primary Examiner*—Francisco Prats
(74) *Attorney, Agent, or Firm*—James B. Bechtel, Esq.; Matthew J. Bussan, Esq.; Scott R. Boalick, Esq.

(57) ABSTRACT

The present invention includes a method for producing 2,3-dimethyl-2,3-dinitrobutane, particularly in high yields, using a peroxidase enzyme site and reacting propane-2-nitronate at the enzyme under appropriate conditions. Peroxidases such as chloroperoxidase, soybean peroxidase and horseradish peroxidase are used. High yields include those amounts that increasingly aid in the manufacture of commercial quantities of 2,3-dimethyl-2,3-dinitrobutane.

18 Claims, 4 Drawing Sheets

2,3-dimethyl-2,3-dinitrobutane (DMDNB)

Peroxidase-catalyzed synthesis of DMDNB; R= $(CH_3)_2CNO_2$.

METHOD FOR PRODUCING 2,3-DIMETHYL-2,3-DINITROBUTANE AND PRODUCT THEREBY

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

1. Field of the Invention

The present invention relates to a method having a peroxidase-catalyzed synthesis from which propane-2-nitronate is reacted at such site, producing 2,3-dimethyl-2,3-dinitrobutane, and the product thereby. The present invention also relates to a method for producing high yields of 2,3-dimethyl-2,3-dinitrobutane, and product thereby.

2. Brief Description of the Related Art 2,3-dimethyl-2,3-dinitrobutane (DMDNB) is a volatile detection agent used as an additive for explosives.

SUMMARY OF THE INVENTION

The present invention includes a method for producing high yields of 2,3-dimethyl-2,3-dinitrobutane comprising the steps of providing a peroxidase enzyme, oxidizing the peroxidase enzyme with a peroxide and reacting propane-2-nitronate at such oxidated site, wherein 2,3-dimethyl-2,3-dinitrobutane is produced. Peroxidase such as chloroperoxidase, soybean peroxidase and horseradish peroxidase may be used. High yields are preferably produced which include those amounts that increasingly aid in the manufacture of commercial quantities of 2,3-dimethyl-2,3-dinitrobutane. The present invention further includes the 2,3-dimethyl-2,3-dinitrobutane product produced by the methods taught herein.

DETAILED DESCRIPTION OF THE PREFERRED EMBODIMENT

Figure 1:
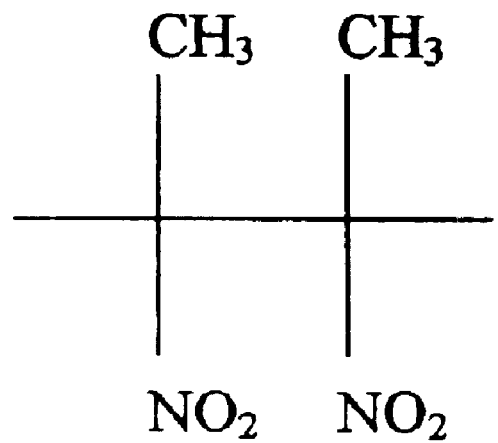
FIG. 1 shows the chemical structure for 2,3-dimethyl-2,3-dinitrobutane.

It has been unexpectedly discovered that high yields of 2,3-dimethyl-2,3-dinitrobutane (DMDNB) may be produced from a peroxidase-catalyzed synthesis. The present invention includes a method for the production of high yields of 2,3-dimethyl-2,3-dinitrobutane, and the 2,3-dimethyl-2,3-dinitrobutane product thereby. The chemical structure of DMDNB is shown in FIG. 1.

DMDNB, in high yields, results from a method that includes the steps of providing a peroxidase enzyme, oxidizing the peroxidase enzyme with a peroxide and reacting propane-2-nitronate at such oxidated site, producing 2,3-dimethyl-2,3-dinitrobutane.

The peroxidases include for example, without limitation, chloroperoxidase (CPO), soybean peroxidase (SBP) and horseradish peroxidase (HRP), which are isolated from plants and microbes. These peroxidases are commercially available redox enzymes that catalyze the oxidative transformations of organic substrates. Chloroperoxidase is available from Sigma-Aldrich of St. Louis, Mo. under the tradename "Chloroperoxidase from *Caldariomyces fumago*," soybean peroxidase is available from Sigma-Aldrich of St. Louis, Mo. under the tradename "Lectin, Peroxidase labeled from *Glycine max* (soybean)" and horseradish peroxidase is available from Sigma-Aldrich of St. Louis, Mo. under the tradename "Peroxidase from Horseradish." Other peroxides include, for example, lactoperoxidase.

Figure 2:
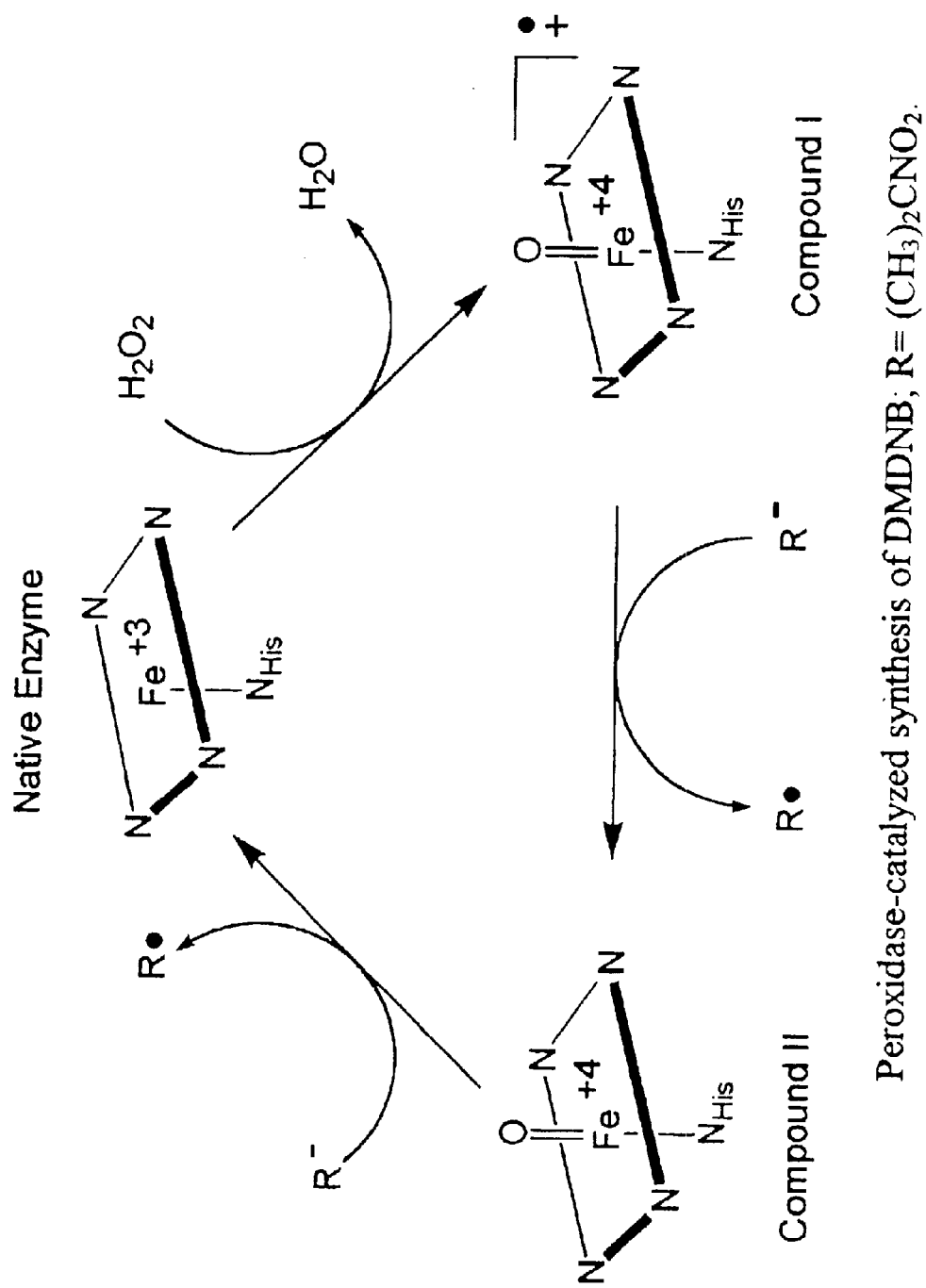
FIG. 2 shows a possible DMDNB synthesis through peroxidase-catalysis synthesis.

Although not wanting to be bound by theory, DMDNB catalysis synthesis through the active site of the peroxidase is believed to occur as shown in FIG. 2, which shows peroxidase-catalyzed synthesis of DMDNB with R=(CH$_3$)$_2$CNO$_2$. The first step in the catalytic cycle is a two-electron oxidation of the resting high-spin Fe$^{III}$ native enzyme by H$_2$O$_2$ to give a species identified as "Compound I" and H$_2$O as a byproduct. The formal oxidation state of Compound I is Fe$^V$, although experimental evidence suggests it is most likely a highly delocalized Fe$^{IV}$ porphyrin radical cation. Compound I then proceeds to abstract an electron from propane-2-nitronate to generate the corresponding 2-nitropropyl radical and Compound II. Compound II subsequently abstracts an electron from another propane-2-nitronate molecule to generate another free radical and regenerate native peroxidase. The ensuing radicals then diffuse into the reaction medium and couple to produce DMDNB.

Figure 3:
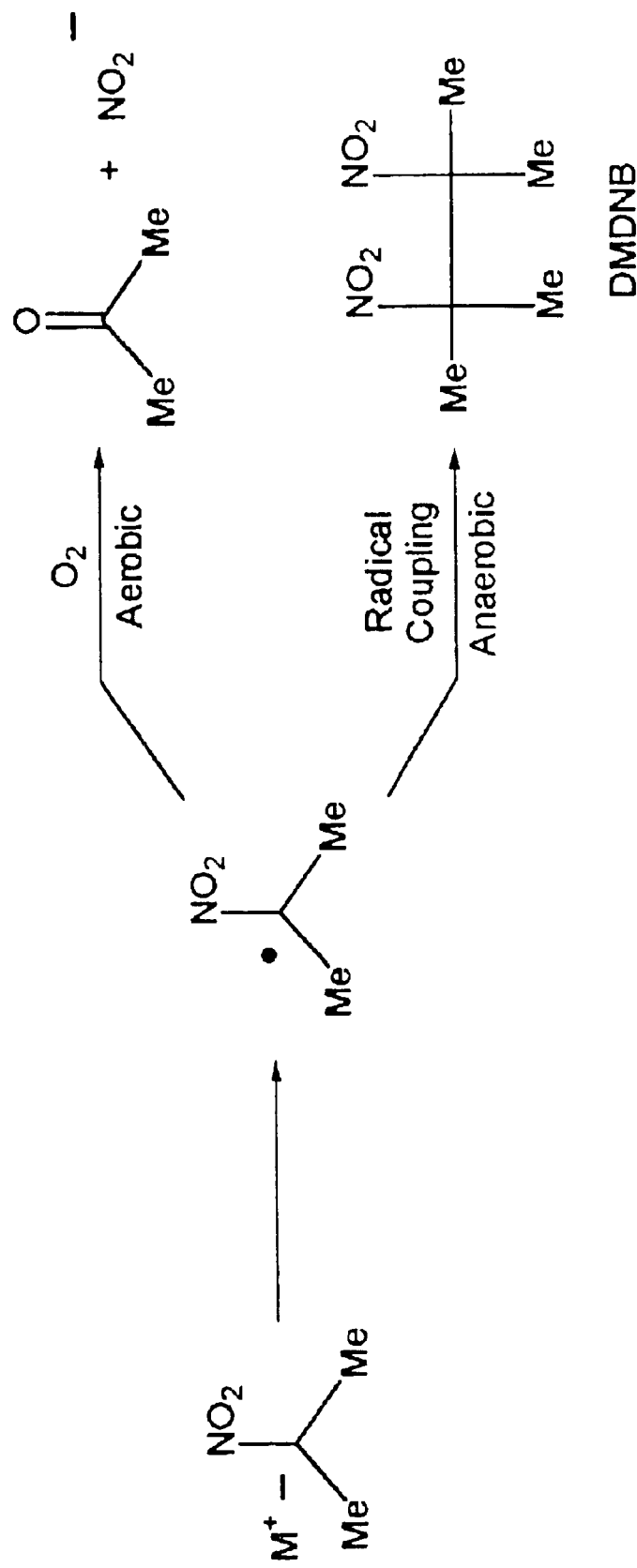
FIG. 3 represents the reaction of peroxidases with 2-nitropropane having two 2-nitropropane molecules couple to form DMDNB under anaerobic conditions, while oxygen and propane-2-nitronate react to form acetone under aerobic conditions; and, FIG. 4 is a graph of the percent yield of DMDNB over a pH range of 3.5 to 7.

Peroxidases catalysts do not require expensive cofactors to facilitate the transformation of propane-2-nitronate to 2,3-dimethyl-2,3-dinitrobutane while being relatively stable and capable of accepting a wide range of substrates. The peroxidases are capable of oxidatively coupling two 2-nitropropane molecules together to form DMDNB. Under aerobic conditions, peroxidase activated with H$_2$O$_2$ utilizes propane-2-nitronate to give acetone, while under anaerobic conditions DMDNB is produced, as seen in FIG. 3.

The propane-2-nitronate may be formed by any appropriate reaction, as known in the art. Preferably, the propane-2-nitronate is formed from the step of reacting 2-nitropropane with an ionizing compound. 2-nitropropane is commercially available from Sigma-Aldrich of St. Louis, Mo. under the tradename "2-nitropropane." Ionizing compounds may include those compounds that ionize 2-nitropropane to propane-2-nitronate. Such ionizing compounds, include without limitation, potassium acetate, potassium hydroxide, sodium acetate, sodium hydroxide, lithium acetate, lithium hydroxide, and the like. When the propane-2-nitronate is formed from the reaction of 2-nitropropane with an ionizing compound, the 2-nitropropane and ionizing compound are preferably present in equimolar amounts, or amounts close thereto. Once combined, the 2-nitropropane and ionizing compound are sufficiently combined, such as mixing, stirring or other like agitative methods for a period of time that allows a single phase, comprising propane-2-nitronate, to form. Such periods of time include from about one hour or more, more preferably from about two hours to about four hours, and most preferably from about two hours to about three hours.

Reaction of the propane-2-nitronate at the peroxidase activation reaction site occurs in the presence of an oxidant, such as a peroxide. The peroxide may include without limitation, hydrogen peroxide, lithium peroxide, sodium peroxide, calcium peroxide, potassium superoxide ($KO_2$) and the like. Hydrogen peroxide is preferred. The peroxide may be present in any suitable amount for the yield desired. Preferably the peroxide is present in an amount greater than the amount of propane-2-nitronate, including such as from about 1.5 times or more greater, about 2 times or more greater, about 3 times or more greater, about 5 times or more greater, about 10 times or more greater, about 20 times or more greater, about 50 times or more greater, about 100 times or more greater, about 500 times or more greater, about 1000 times or more greater, about 10,000 times or more greater, etc. than the propane-2-nitronate.

Reaction of the propane-2-nitronate preferably occurs in an aqueous medium comprising water. Other mediums may be used, such as organic solvents isopropyl alcohol, ethanol, acetone and the like.

The reacting propane-2-nitronate occurs at an appropriate pH for the production of high DMDNB yields. The pH preferably ranges from about 3.5 to less than about 5.0, more preferably from 3.6 to about 4.8, still more preferably from about 3.8 to about 4.5, and most preferably from about 3.9 to about 4.3. Temperatures of the reaction are preferably ambient temperature for economical production of the DMDNB, but may be varied, more preferably increased, as determined by those skilled in the art, with a temperature range of from about 25° C. to about 37° C. preferred.

The peroxide is added to the reaction in a ratio suitable for high yields of DMDNB, preferably from about 25,000 to about 75,000 parts peroxide to about 1 part peroxidase per hour, more preferably from about 35,000 to about 65,000 parts peroxide to about 1 part peroxidase per hour, and most preferably in an amount of about 50,000 parts peroxide to about 1 part peroxidase per hour.

Once formed the DMDNB precipitates out of solution as a white precipitate. The precipitate may be collected by vacuum filtration or other appropriate method of extraction.

The present invention produces a high yield of 2,3-dimethyl-2,3-dinitrobutane, which include those amounts suitable for commercial manufacture of DMDNB. High yields include for example from about 35% or more yield, from about 40% or more yield, about 50% or more yield, about 60% or more yield, about 65% or more yield, about 70% or more yield, etc. Percentage yield is based on the equivalent amount of 2,3-dimethyl-2,3-dinitrobutane to the substrate 2-nitropropane. High yields are preferably produced which include those amounts that increasingly aid in the manufacture of commercial quantities of 2,3-dimethyl-2,3-dinitrobutane.

The 2,3-dimethyl-2,3-dinitrobutane produced by the method of the present invention is suitable for use as an explosive additive for detection purposes.

As the efficiency of the reaction approaches 100%, the only byproduct formed during this reaction is water. At lower efficiencies other byproducts, such as acetone, acetoxime, and 2-nitropropane, are also generated during the reaction. The 2-nitropropane and acetoxime are formed at low levels. The 2-nitropropane, produced by reprotonation of the corresponding nitronate anion, may be recovered and recycled for use in subsequent reactions. Minimization of the unwanted side reactions that produce acetone allows the propane-2-nitronate substrate to be better utilized by the peroxidase, and thereby, improving the DMDNB yield even further. As such these side reactions are generally minimized, such as by oxygen displacement or removal.

Such methods for the reduction of oxygen content of the reaction solution may include bubbling an inert gas, such as nitrogen gas or argon gas, through the reaction solution, using an enzyme which maintains an oxygen-free environment in solution such as a commercial product sold under the tradename Oxyrase®, manufactured by Oxyrase Inc. of Oakridge, Tenn., using selective oxygen chelators, and like methods of lowering the oxygen content as determinable by those skilled in the art. Oxygen chelators, include, without limitation, thioglycolic acid or sodium dithionite. Generally, the catalyzed synthesis is optimized for continuing higher yields and lower production cost of the DMDNB.

EXAMPLE 1

Equimolar amounts of potassium hydroxide and 2-nitropropane were dissolved in water to achieve final concentrations of 2.32 M each. The two liquids were combined into one vessel and stirred for 3.5 hours at a temperature of approximately 25° C., resulting in a single phase of 2.32 M propane-2-nitronate. Potassium hydroxide and hydrochloric acid were added to adjust the pH of solution to about 4.0. Horseradish peroxidase was added to the solution to attain a concentration of $7.68 \times 10^6$ M horseradish peroxidase. Hydrogen peroxide and water (7 ml of 30% hydrogen peroxide in water) were added to the single phase solution dropwise over a period of about 2.5 hours to attain a solution that is 10.7 M hydrogen peroxide and 0.096 M propane-2-nitronate. The solution was then stirred for approximately 2.5 hours. A white precipitate formed with each drop addition and collected at the bottom of the reaction vessel. A vacuum filter was used to collect white powder.

The white powder was identified as DMDNB by dissolving it in acetone and comparing with DMDNB (purchased from Sigma-Aldrich of St. Louis, Mo. under the tradename "2,3-dimethyl-2,3-dinitrobutane") dissolved in acetone through gas chromatography and FT-IR. The yield of Example 1 was approximately 73.6% (equivalent DMDNB/equivalent 2-nitropropane).

EXAMPLE 2

The procedure of Example 1 was followed with the exception that the pH was approximately 4.5 and only water (i. e., no hydrogen peroxide) was added. The yield was 0%.

EXAMPLE 3

The procedure of Example 1 was followed with the exception that the pH was approximately 4.5 and a total of 14 ml of 15% hydrogen peroxide in water was added at 3 ml/hr. The yield was 11.7%.

Figure 4:
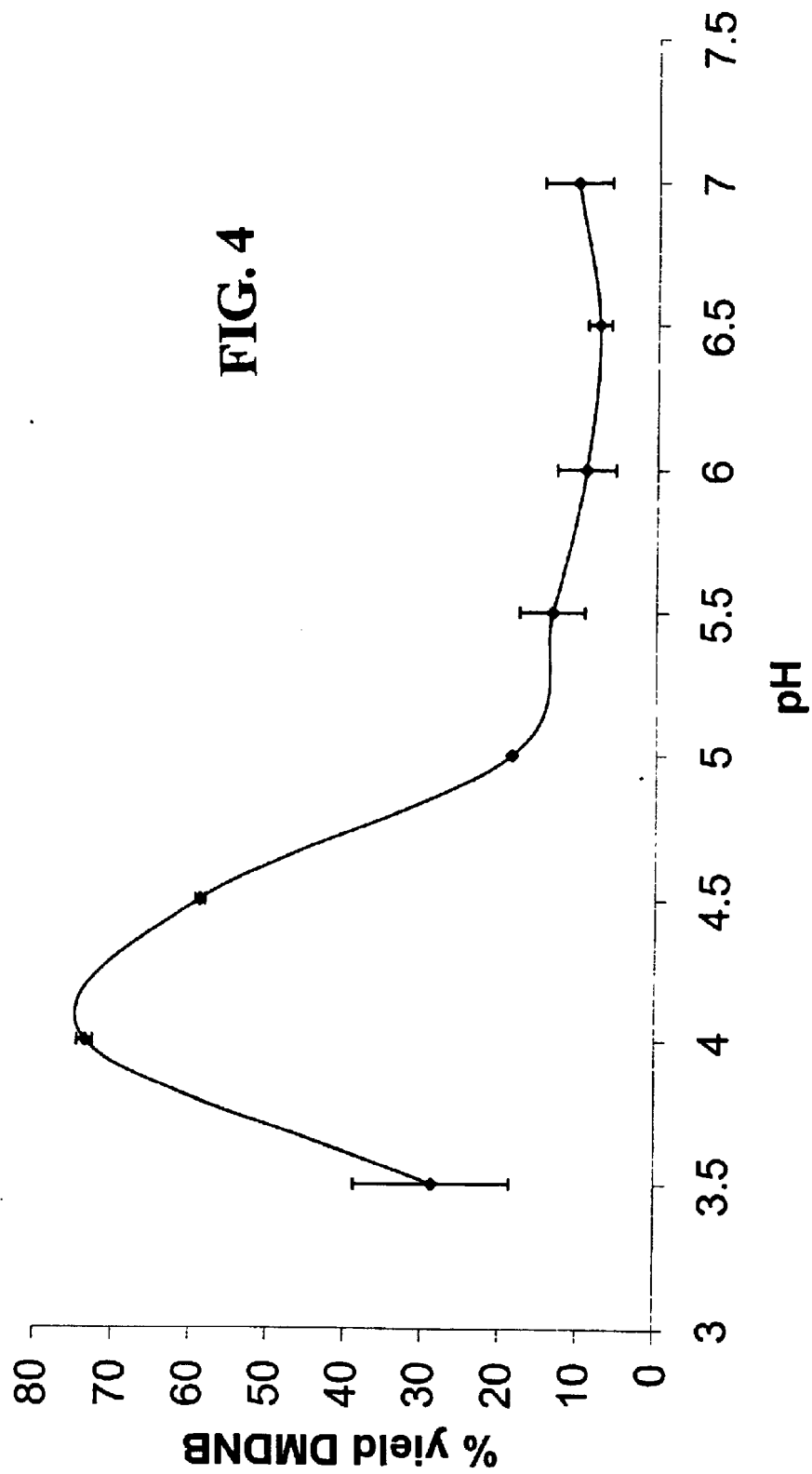

Examples 4–11 are experiments over a pH range of 3.5 to 7.0 using HRP. A graphical representation of the combined results of these examples is shown in FIG. 4.

EXAMPLE 4

The procedure of Example 1 was followed (twice) with the exception that the pH was approximately 3.5. The average yield was 28.7% (21.6% and 35.8%, with a standard deviation of 10).

EXAMPLE 5

The procedure of Example 1 was followed (twice) with the exception that the pH was approximately 4.0. The average yield was 73.6% (74.3% and 72.9%, with a standard deviation of 1).

EXAMPLE 6

The procedure of Example 1 was followed (thrice) with the exception that the pH was approximately 4.5. The average yield was 58.83% (58.2%, 589.5% and 58.8%, with a standard deviation of 1).

EXAMPLE 7

The procedure of Example 1 was followed (twice) with the exception that the pH was approximately 5.0. The average yield was 18.6% (18.6% and 18.6%, with a standard deviation of 0).

EXAMPLE 8

The procedure of Example 1 was followed (twice) with the exception that the pH was approximately 5.5. The average yield was 13.5% (16.5% and 10.5%, with a standard deviation of 4).

EXAMPLE 9

The procedure of Example 1 was followed (twice) with the exception that the pH was approximately 6.0. The average yield was 9.2% (11.9% and 6.5%, with a standard deviation of 4).

EXAMPLE 10

The procedure of Example 1 was followed (twice) with the exception that the pH was approximately 6.5. The average yield was 7.5% (6.5% and 8.6%, with a standard deviation of 1).

EXAMPLE 11

The procedure of Example 1 was followed (twice) with the exception that the pH was approximately 7.0. The average yield was 10.4% (7.3% and 13.5%, with a standard deviation of 4).

The foregoing summary, description, and examples of the present invention are not intended to be limiting, but are only exemplary of the inventive features which are defined in the claims.

What is claimed is:

1. A method for producing high yields of 2,3-dimethyl-2,3-dinitrobutane of at least 35%, comprising the steps of:
    providing a peroxidase enzyme;
    oxidizing the peroxidase enzyme with a peroxide; and,
    reacting propane-2-nitronate at such oxidated site at a pH of from about 3.5 to less than 5.0, wherein 2,3-dimethyl-2,3-dinitrobutane is produced.

2. The method of claim 1, wherein the peroxidase enzyme is selected from the group consisting of horseradish peroxidase, soybean peroxidase and chloroperoxidase.

3. The method of claim 2, wherein the peroxidase enzyme comprises horseradish peroxidase.

4. The method of claim 2, wherein the peroxidase enzyme comprises soybean peroxidase.

5. The method of claim 2, wherein the peroxidase enzyme comprises chloroperoxidase.

6. The method of claim 1, wherein the peroxide is selected from the group consisting of hydrogen peroxide, lithium peroxide, sodium peroxide, calcium peroxide and potassium superoxide.

7. The method of claim 6, wherein the peroxide comprises hydrogen peroxide.

8. The method of claim 1, wherein the peroxide is added to the reaction in a ratio of from about 25,000 to about 75,000 parts peroxide to about 1 part peroxidase per hour.

9. The method of claim 8, wherein the ratio ranges from about 35,000 to about 65,000 parts peroxide to about 1 part peroxidase per hour.

10. The method of claim 9, wherein the ratio is present in an amount of about 50,000 parts peroxide to about 1 part peroxidase per hour.

11. The method of claim 1, wherein the pH ranges from 3.6 to about 4.8.

12. The method of claim 11, wherein the pH ranges from about 3.8 to about 4.5.

13. The method of claim 12, wherein the pH ranges from about 3.9 to about 4.3.

14. The method of claim 1, wherein the step of reacting propane-2-nitronate at such oxidated site occurs at a temperature of from about 25° C. to about 37° C.

15. The method of claim 1, wherein the final yield of 2,3-dimethyl-2,3-dinitrobutane produced ranges from about 50% or greater.

16. The method of claim 15, wherein the final yield of 2,3-dimethyl-2,3-dinitrobutane produced ranges from about 65% or greater.

17. A method for producing high yields of 2.3-dimethyl-2 3-dinitrobutane of at least 35% comprising the steps of:
    providing a peroxidase enzyme;
    oxidizing the peroxidase enzyme with a peroxide; and,
    reacting propane-2-nitronate at such oxidated site at a pH of from about 3.5 to less than 5.0, wherein 2,3-dimethyl-2,3-dinitrobutane is produced,
    wherein the final yield of 2,3-dimethyl-2,3-dinitrobutane produced comprises about 70%.

18. A method for producing high yields of 2,3-dimethyl-2,3-dinitrobutane of at least 35% to about 73.6%, comprising the steps of:
    providing a peroxidase enzyme;
    oxidizing the peroxidase enzyme with a peroxide; and,
    reacting propane-2-nitronate at such oxidated site at a pH of from about 3.5 to less than 5.0, wherein 2,3-dimethyl-2,3-dinitrobutane is produced.

* * * * *